United States Patent
Yeh et al.

(10) Patent No.: US 9,260,405 B2
(45) Date of Patent: Feb. 16, 2016

(54) CAYALYST SYSTEM AND MANUFACTURING METHOD OF CYCLIC CARBONATE BY THE SAME

(71) Applicant: Industrial Technology Research Institute, Hsinchu (TW)

(72) Inventors: Cheng-Wei Yeh, Pingtung County (TW); Mao-Lin Hsueh, Pingtung County (TW); Yi-Zhen Chen, Tainan (TW); Chih-Wei Liu, Hualien County (TW); Kuo-Chen Shih, Kaohsiung (TW); Hsi-Hsin Shih, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 44 days.

(21) Appl. No.: 14/140,479

(22) Filed: Dec. 25, 2013

(65) Prior Publication Data

US 2015/0119584 A1    Apr. 30, 2015

(30) Foreign Application Priority Data

Oct. 24, 2013  (TW) .............................. 102138524 A

(51) Int. Cl.
  *C07D 317/34*  (2006.01)
  *B01J 27/14*   (2006.01)
  *B01J 27/24*   (2006.01)

(52) U.S. Cl.
  CPC ............... *C07D 317/34* (2013.01); *B01J 27/14* (2013.01); *B01J 27/24* (2013.01)

(58) Field of Classification Search
  CPC .................................................... C07D 317/34
  See application file for complete search history.

(56) References Cited

U.S. PATENT DOCUMENTS

| | | | |
|---|---|---|---|
| 5,153,333 A | 10/1992 | Schubert et al. | |
| 6,156,909 A | 12/2000 | Kim et al. | |
| 6,218,564 B1 | 4/2001 | Monteith | |
| 6,407,264 B2 | 6/2002 | Kim et al. | |
| 7,145,029 B2 | 12/2006 | Schlosberg et al. | |
| 7,365,214 B2 | 4/2008 | Srinivas et al. | |
| 7,488,835 B2 | 2/2009 | Van Kruchten et al. | |
| 2002/0013477 A1 | 1/2002 | Kim et al. | |
| 2004/0192803 A1 | 9/2004 | Figovsky et al. | |
| 2004/0236136 A1 | 11/2004 | Schlosberg et al. | |
| 2005/0070724 A1 | 3/2005 | Srinivas et al. | |

FOREIGN PATENT DOCUMENTS

| | | |
|---|---|---|
| CN | 101270112 A | 9/2008 |
| CN | 101474576 A | 7/2009 |
| CN | 101811067 A | 8/2010 |
| CN | 102076651 | 5/2011 |
| EP | 1490323 A1 | 12/2004 |
| JP | 2006104092 | 4/2006 |
| JP | 2006151891 A | 6/2006 |
| JP | 2010207814 | 9/2010 |

OTHER PUBLICATIONS

Office Action of Taiwan Counterpart Application, issued on Dec. 8, 2014, p. 1-p. 4, in which the listed references were cited.
Donald J. Darensbourg, et al., "Copolymerization of CO2 and Epoxides Catalyzed by Metal Salen Complexes," Accounts of Chemical Research, vol. 37, No. 11, May 27, 2004, pp. 1-9.
Shui-Sheng Wu, et al., "ZnBr2—Ph4PI as highly efficient catalyst for cyclic carbonates synthesis from terminal epoxides and carbon dioxide," Applied Catalysis A: General, Mar. 10, 2008, pp. 106-111.
Jinliang Song, et al., "Highly efficient synthesis of cyclic carbonates from CO2 and epoxides catalyzed by KI/lecithin," Catalysis Today, Sep. 23, 2011, pp. 130-135.
Michael R. Kember, et al., "Catalysts for CO2/epoxide copolynnerisation," The Royal Society of Chemistry, Sep. 16, 2010, pp. 141-163.
Joachim E. Dengler, et al., "A One-Component Iron Catalyst for Cyclic Propylene Carbonate Synthesis," European Journal of Inorganic Chemistry, Dec. 14, 2010, pp. 336-343.

*Primary Examiner* — Noble Jarrell
*Assistant Examiner* — John S Kenyon
(74) *Attorney, Agent, or Firm* — Jianq Chyun IP Office

(57) ABSTRACT

A catalyst system and a method for manufacturing cyclic carbonate by the same are provided. The catalyst system includes a transition metal salt containing a halo group, an acetate group, or a combination thereof, and an organic phosphine ligand. The molar ratio of the organic phosphine ligand to the transition metal salt is greater than 0 and less than or equal to 50.

11 Claims, No Drawings

CAYALYST SYSTEM AND MANUFACTURING METHOD OF CYCLIC CARBONATE BY THE SAME

CROSS-REFERENCE TO RELATED APPLICATION

This application claims the priority benefit of Taiwan application serial no. 102138524, filed on Oct. 24, 2013. The entirety of the above-mentioned patent application is hereby incorporated by reference herein and made a part of this specification.

TECHNICAL FIELD

The disclosure relates to a catalyst system and a manufacturing method of cyclic carbonate with the catalyst system.

BACKGROUND

In the resin industry, a resin having a cyclic carbonate functional group may be used in the synthesis of non-isocyanate polyurethane resin (NIPU), and the isocyanate compounds having higher toxicity are abrogated from being applied in the synthesizing process. In the industry, the isocyanate monomer is produced using phosgene, in which both the raw materials and the end products are highly toxic chemicals. Accordingly, greener materials, for replacing the isocyanate polyurethane resin material, gradually become the focus of attention. Since the non-isocyanate material do not have moisture sensitive isocyanate functional groups, the storage and processing conditions are preferred over those of a conventional polyurethane resin.

The critical material for the non-isocyanate polyurethane resin is a cyclic carbonate compound, which is prepared by using carbon dioxide and an epoxy compound. The method of synthesis includes utilizing a Lewis base, an ionic liquid, a metal complex, a heterogeneous metal salt, a silica supported catalyst, an oxidized metal salt porous material or an ion exchange resin as a catalytic system to catalyze the reaction of carbon dioxide and the epoxy compound. Among the above catalysts, the salt type or the ionic liquid catalyst is the most commonly used. However, these catalysts are usually less soluble in an epoxy compound. Consequently, the amount of catalyst used is increased and the reaction conditions are adjusted to high temperature and high pressure in order to achieve the desired conversion rate. Further, by-products are generated. Alternatively, ligands synthesized through special designs or expensive metal ions may be utilized to prepare the catalyst. However, not only commercial production becomes difficult, the product cost increases and the recycling of catalyst is inevitable. Due to above reasons, the bar of the fabrication technology of cyclic carbonate is raised, and the yield of non-isocyanate polyurethane resin cannot be effectively improved.

Accordingly, the development of a new generation of catalyst system having high reaction activity, being producible under moderate reaction conditions, being able to preclude the requisite of being recycled from the product and being cost-effective has become the focus of attention in the fabrication technology of cyclic carbonate.

SUMMARY

An exemplary embodiment of the disclosure provides a catalyst system that includes a transition metal salt and an organic phosphine ligand, wherein the transition metal salt includes a halo group, an acetate group, or a combination thereof. The molar ratio of the organic phosphine ligand to the transition metal salt is greater than 0 and less than or equal to 50.

An exemplary embodiment of the disclosure provides a manufacturing method of cyclic carbonate. An epoxy compound and carbon dioxide are supplied to a reactor to be in contact with the above-mentioned catalyst system to form a cyclic carbonate compound. Based on the amount of the epoxy compound used as a calculation standard, the amount of the catalyst system used is 1 mmol % to 50 mmol %.

In the following detailed description, for purposes of explanation, numerous specific details are set forth in order to provide a thorough understanding of the disclosed embodiments. It will be apparent, however, that one or more embodiments may be practiced without these specific details.

DETAILED DESCRIPTION OF DISCLOSED EXEMPLARY EMBODIMENTS

In one exemplary embodiment of the disclosure, the catalyst system includes a transition metal salt and an organic phosphine ligand. The transition metal salt includes at least a halo group, an acetate group or a combination thereof. The molar ratio of the above-mentioned organic phosphine ligand to the above-mentioned transition metal salt may be greater than 0 but less than or equal to 50, for example, greater than 0 but less than or equal to 8. If the ratio of the organic phosphine ligand is too high, the organic phosphine ligand may not be effectively dispersed in the system, and the subsequent application of the cyclic carbonate is adversely affected. Further, the above-mentioned catalytic system may also contain a halogen-containing compound, and the molar ratio of the above-mentioned halogen-containing compound to the transition metal salt may be greater than 0 but less than or equal to 50, for example, greater than 0 but less than or equal to 10. If the ratio of the above-mentioned halogen-containing compound is too high, the halogen-containing compound may not be effectively dispersed in the system, and the subsequent application of the cyclic carbonate is affected.

In an exemplary embodiment, the above-mentioned transition metal salt includes halogen-containing transition metal salt, such as $CoBr_2$, $RhCl_3$, $RuCl_2$, $FeCl_2$. Other effective halogen-containing transition metal salt may include $PdX_n$ (palladium halides, since valance varies, halides are represented by the general formula $X_n$), $FeCl_3$, $AlCl_3$, $TiCl_4$, $ScX_2$, $ScX_3$ (scandium halides), $VX_n$ (vanadium halides), $ZnX_2$ (zinc halides), $CuX_2$ (copper halides), tin halides ($SnX_2$), $ZrX_n$ (zirconium halides), $MoX_n$ (molybdenum halides), $WX_n$ (tungsten halides), $PtX_n$ (pallatinum halides), $BiX_n$ (bismuth halides), etc, wherein X represents chlorine, bromine, or iodine; n is greater than 1 and less than or equal to 6, commonly 2 or 4 according to valence number.

In another exemplary embodiment, the above-mentioned transition metal salt includes a transition metal salt containing an acetate group, such as $Co(OAc)_2$, $Zn(OAc)_2$, $Pd(OAc)_2$, $Fe(OAc)_2$, $Fe(OAc)_3$, $Cu(OAc)_2$, $Cs(OAc)$, $Rh(OAc)_2$ (dimer), $Pb(OAc)_2$, $Sb(OAc)_3$, $La(OAc)_3$, $Bi(OAc)_3$, $Cd(OAc)_2$, $Y(OAc)_3$, $Sc(OAc)_3$, or $Sc(OTf)_3$ (scandium triflate).

In one exemplary embodiment, the above-mentioned halogen-containing compound includes, but not limited to, tetrabutylammonium chloride, (TBAC), anilinium chloride, benzalkonium chloride, benzoxonium chloride, cetrimonium chloride, cetylpyridinium chloride, choline chloride, didecyl dimethyl ammonium chloride, dimethyl dioctadecyl ammonium chloride, stearalkonium chloride, tetramethyl ammonium chloride, tetrabutylammonium bromide (TBAB), tetrabutylammonium iodide (TBAI), tetraethylammonium bromide, domiphen bromide, benzododecinium bromide, (1-ethoxy-1-oxohexadecan-2-yl)-trimethylazanium bromide, cetrimonium bromide, emepronium bromide, tetrabutylammonium tribromide, tetraoctylammonium bromide, thonzonium bromide, dithiazanine iodide, methiodide, or tetraethylammonium iodide.

In one exemplary embodiment, the above-mentioned organic phosphine ligand includes, but not limited to, triphenyl phosphine ($PPh_3$), triphenyl phosphine oxide ($OPPh_3$), Poly(dipropylene glycol) phenyl phosphite, tricyclohexyl phosphine ($PCy_3$), Tris(2,4-di-tert-butylphenyl)phosphite, triphenyl phosphite, or diphenylmethyl phosphine.

In one exemplary embodiment, the molar ratio of above-mentioned organic phosphine ligand to the transition metal salt is not particularly limited, as long as it is greater than 0, for example, greater than 0 but less than or equal to 50. In another example, the molar ratio may be greater than 0 but less than or equal to 8. The molar ratio of the above-mentioned halogen-containing compound to the cobalt in the transition metal salt is not particular limited, as long as it is greater than 0, for example, greater than 0 but less than or equal to 50. In another example, the molar ratio may be greater than 0 but less than or equal to 10.

The fabrication method according to an exemplary embodiment includes rendering an epoxy compound and carbon dioxide to be in contact with the above-mentioned catalyst system in a reactor to form a cyclic carbonate compound. The epoxy compound of the embodiment may include any typical epoxy compound used in the preparation of a cyclic carbonate compound and is not particularly limited. The epoxy compound of the embodiment may include, but not limited to, 1,4-butanediol diglycidyl ether (BDGE), 1,4-cyclohexanedimethanol diglycidyl ether (a mixture of trans and cis, CHDDG), trimethylolpropane triglycidyl ether (TMPTGE), etc. Further, based on the amount of the epoxy compound used as a calculation standard, the amount of the catalyst system used may be between 1 mmol % to 50 mmol %, for example, between 1 mmol % to 10 mmol %. It is not beneficial to the reaction if too much catalyst is being used. In this exemplary embodiment, the reaction temperature is lower than 100° C., for example, greater than room temperature but lower than 100° C., for example, between 50° C. to 90° C. If the temperature is too low, the reaction time is extended in order to achieve the preferred cyclic carbonate conversion rate. The pressure of carbon dioxide is between 1 to 20 atm, for example, between 1 to 10 atm. If the pressure is too high, the required equipment specifications have to be strict and the production of cyclic carbonate will not be economical. The reaction time may be between 1 to 20 hours, for example, between 1 to 8 hours. It is not beneficial to the conversion rate if the reaction time is too long.

In the above exemplary embodiment, a cyclo-addition reaction occurs when the catalyst system comprising transition metal salt and organic phosphine ligand in the presences of carbon dioxide and an epoxy compound. The catalyst system may further include halogen-containing compound. The catalyst system does not result in the generation of polycarbonate but instead induces the generation of cyclic carbonate. Further, the above-mentioned catalyst system has a more superior and stable chemical activity; using a small amount thereof is sufficient to provide a desired cyclic carbonate conversion rate. The catalyst system of the disclosure provides a cyclic carbonate product with a high conversion rate under moderate reaction conditions.

Several experiments were conducted to demonstrate the effects of the exemplary embodiments of the disclosure. It should be understood that these experiments are presented by way of examples and not by way of limitation.

EXAMPLE 1

An epoxy compound 1,4-butanediol diglycidyl ether (BDGE, cas no. 2425-79-8, 15 g) and cobalt bromide ($CoBr_2$ anhydrous, 81 mg), and triphenyl phosphine ($PPh_3$, 195 mg) were placed in a reactor. The reactor was then sealed and the air inside was drawn out by vacuum. Carbon dioxide was supplied to the reactor. After repeating the above process for three times, carbon dioxide was delivered into the reactor and the pressure of the reactor could reach 8 atm. The mixture was heated to 90° C. and was spun at a rate of 500 rpm. The mixture was allowed to be stirred for 4 hours. The reaction equation of Example 1 is as follow:

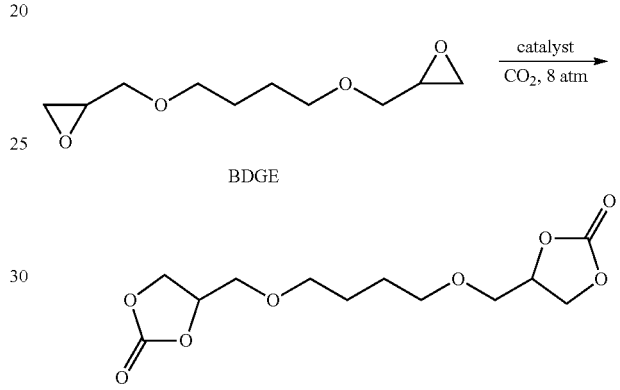

The gas was released from the reactor until atmospheric pressure was reached. The heating was halted for the reactor temperature dropping to room temperature. The product was then removed and the conversion rate of the cyclic carbonate of the product was analyzed by $^1H$ NMR spectrum. The conversion rate of the cyclic carbonate was determined to be 85% and was recorded in Table 1.

EXAMPLE 2

An epoxy compound 1,4-butanediol diglycidyl ether (BDGE, 250 g), Cobalt acetate tetrahydrate ($Co(OAc)_2 \cdot 4H_2O$, 1.54 g), triphenyl phosphine ($PPh_3$, 3.25 g) and (tetrabutylammonium bromide (TBAB, 3.99 g) were placed in a reactor. The reactor was sealed and the air therein was drawn out by vacuum. Carbon dioxide was provided to the reactor. After repeating the above process step for three times, carbon dioxide was delivered into the reactor and the pressure inside the reactor could reach 8 atm. The mixture was then heated to 90° C. and was spun at a rate of 500 rpm. The mixture was allowed to be stirred for 4 hours. The gas was then released from the reactor until atmospheric pressure was reached. Further, the heating was halted for the reactor temperature dropping to room temperature. The product was then removed. The conversion rate of the cyclic carbonate of the product analyzed by $^1H$ NMR spectrum was determined to be greater than 99% and was recorded in Table 1.

EXAMPLE 3

An epoxy compound 1,4-cyclohexanedimethanol diglycidyl ether (CHDDG, a mixture of cis and trans, 15 g), cobalt acetate tetrahydrate, (Co(OAc)$_2$·4H$_2$O, 72 mg), triphenyl phosphine (PPh$_3$, 153 mg) and tetrabutylammonium bromide (TBAB, 189 mg) were placed in a reactor. The reactor was sealed and the air inside was drawn out by vacuum. Carbon dioxide was supplied to the reactor. After repeating the above process for three times, carbon dioxide was delivered into the reactor and the pressure inside the reactor could reach 8 atm. The mixture was then heated to 90° C. and was spun at a rate of 500 rpm. The mixture was stirred for 4 hours. The gas was then released from the reactor until atmospheric pressure was reached. Further, the heating was halted for the reactor temperature dropping to room temperature. The product was subsequently removed. The conversion rate of the cyclic carbonate of the product was analyzed by $^1$H NMR spectrum and was determined to be 78%. The result is recorded in Table 1.

EXAMPLE 4

An epoxy compound trimethylolpropane triglycidyl ether (TMPTGE, 15 g), cobalt acetate tetrahydrate (Co(OAc)$_2$·4H$_2$O, 62 mg) as catalyst, triphenyl phosphine (PPh$_3$, 130 mg) and tetrabutylammonium bromide (TBAB, 160 mg) were placed in a reactor. The reactor was sealed and the air inside was drawn out by vacuum. Carbon dioxide was supplied to the reactor. After repeating the above process for three times, carbon dioxide was delivered into the reactor and the pressure inside the reactor could reach 8 atm. The mixture was then heated to 90° C. and was spun at a rate of 500 rpm. The reaction was conducted for 4 hours. Thereafter, the gas was released from the reactor until atmospheric pressure was reached. Further, the heating was halted for the reactor temperature dropping to room temperature and the product was removed. The conversion rate of the cyclic carbonate of the product was analyzed by $^1$H NMR spectrum and was determined to be 81%. The result is recorded in Table 1.

COMPARATIVE EXAMPLE 1

An epoxy compound 1,4-butanediol diglycidyl ether (15 g) and tetrabutylammonium bromide (239 mg) were placed in a reactor. The reactor was sealed and the reaction was carried out for 4 hours following the process similar to Example 1. The product was then removed at room temperature. The conversion rate of the cyclic carbonate of the product was analyzed by $^1$H NMR spectrum and was determined to be 67%. The result is recorded in Table 1.

COMPARATIVE EXAMPLE 2

An epoxy compound 1,4-butanediol diglycidyl ether (15 g), triphenyl phosphine (PPh$_3$, 195 mg) and tetrabutylammonium bromide (239 mg) were placed in a reactor. The reactor was sealed and the reaction was carried out for 4 hours following the process similar to Example 1. The product was then removed at room temperature. The conversion rate of the cyclic carbonate of the product was analyzed by $^1$H NMR spectrum and was determined to be 68%. The result is recorded in Table 1.

COMPARATIVE EXAMPLE 3

An epoxy compound 1,4-butanediol diglycidyl ether (BDGE, 15 g) and cobalt acetate tetrahydrate (Co(OAc)$_2$·4H$_2$O, 92 mg) were placed in a reactor. The reactor was sealed and a reaction was carried out for 4 hours following the process similar to Example 1. The product was then removed at room temperature. The conversion rate of the cyclic carbonate of the product was analyzed by $^1$H NMR spectrum and was determined to be 0%. The result is recorded in Table 1.

TABLE 1

(the addition amount of Co(OAc)$_2$·4H$_2$O was 10 mmol % of the epoxy compound)

| | Transition Metal Salt | Organic Phosphine Ligand | | Halogen-Containing Compound | | Reaction Temp (° C.) | Conversion Rate (%) |
| --- | --- | --- | --- | --- | --- | --- | --- |
| | | Type | Molar Ratio | Type | Molar Ratio | | |
| Example 1 | CoBr$_2$ | PPh$_3$ | 2 | — | — | 90 | 85 |
| Example 2 | Co(OAc)$_2$ | PPh$_3$ | 2 | TBAB | 2 | 90 | >99 |
| Example 3 | Co(OAc)$_2$ | PPh$_3$ | 2 | TBAB | 2 | 90 | 78 |
| Example 4 | Co(OAc)$_2$ | PPh$_3$ | 2 | TBAB | 2 | 90 | 81 |
| Comparative Example 1 | — | — | — | TBAB | 2 | 90 | 67 |
| Comparative Example 2 | — | PPh$_3$ | 2 | TBAB | 2 | 90 | 68 |
| Comparative Example 3 | Co(OAc)$_2$ | — | — | — | — | 90 | 0 |

According to the results summarized in Table 1, the catalyst system of the exemplary embodiments of the disclosure provided a better conversion rate of cyclic carbonate. Further, the application of a substantial amount of catalyst or solvent was also precluded.

PRACTICAL EXAMPLE

The product of example 1 (BDCE, 1,4-butanediol dicarbonate ether, 2.61 g) and epoxy resin monomer 1010 (bisphenol A diglycidyl ether, 3.06 g) were mixed evenly as agent A. Further, m-xylenediamine (2.45 g) and tripentyl amine (10 mg) were evenly mixed as agent B. The above agent A and agent B were mixed evenly in an aluminum plate and the resulting mixture was placed at room temperature for 48 hours for the mixture to solidify. The reactants of the practical example are as shown below:

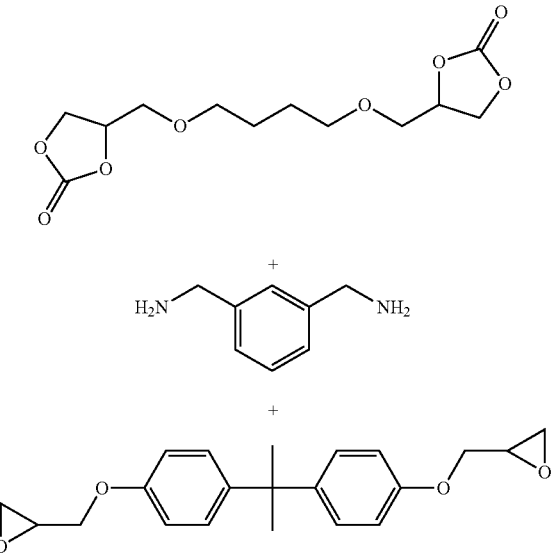

The product obtained was measured using Shore A durometer and the hardness was determined to be 83. Accordingly, it was confirmed that the catalyst system of the disclosure could be used to synthesize a polycarbonate resin product.

The effects of the ratio of each component in the catalyst system on the conversion rates are described in the following Examples 5 to 9.

EXAMPLES 5 to 9

An epoxy compound (1,4-butanediol diglycidyl ether, BDGE, 15 g), cobalt acetate tetrahydrate ($Co(OAc)_2 \cdot 4H_2O$, 92 mg, 10 mmol %), triphenyl phosphine ($PPh_3$) and tetrabutylammonium bromide (TBAB) were placed in a reactor, followed by sealing the reactor. The ratio of triphenyl phosphine ($PPh_3$) to cobalt and the ratio of tetrabutylammonium bromide (TBAB) to cobalt were different in different Examples, as shown in Table 2. Similar to the above Example 1, the reaction was carried out for 4 hours and the product was removed from the reactor after the reactor had return to room temperature and atmospheric pressure. The conversion rate of the cyclic carbonate of the product was analyzed by $^1H$ NMR spectrum and the result is recorded in Table 1.

TABLE 2

(the addition amount of $Co(OAc)_2 \cdot 4H_2O$ was 10 mmol % of the epoxy compound)

| Example | Organic Phosphine Ligand Type | Molar Ratio | Halogen-Containing Compound Type | Molar Ratio | Reaction Temp (° C.) | Conversion Rate (%) |
|---|---|---|---|---|---|---|
| 5 | $PPh_3$ | 2 | TBAB | 2 | 90 | >99 |
| 6 | $PPh_3$ | 8 | TBAB | 2 | 90 | 91 |
| 7 | $PPh_3$ | 2 | TBAB | 2 | 90 | 96 |
| 8 | $PPh_3$ | 1 | TBAB | 2 | 90 | 91 |
| 9 | $PPh_3$ | 2 | TBAB | 10 | 90 | >99 |

According to Table 2, with the ratios of the organic phosphine ligand or the halogen-containing compound of the catalyst system of this disclosure varying, desired conversion rates of cyclic carbonate were nevertheless achieved.

The effects of reaction temperature on the conversion rate of cycle carbonate are described in Example 5 and Example 10 below.

EXAMPLE 10

Aside from the reaction temperature, the composition and the process performed of Example 10 were similar to those of Example 5. The product was removed from the reactor at atmospheric pressure and room temperature. The conversion rate of the cyclic carbonate of the product was analyzed by $^1H$ NMR spectrum and is recorded in Table 3.

TABLE 3

(the addition amount of $Co(OAc)_2 \cdot 4H_2O$ was 10 mmol % of the epoxy compound)

| Example | Organic Phosphine Ligand Type | Molar ratio | Halogen-Containing Compound Type | Molar Ratio | Reaction Temp (° C.) | Conversion Rate (%) |
|---|---|---|---|---|---|---|
| 5 | $PPh_3$ | 2 | TBAB | 2 | 90 | >99 |
| 10 | $PPh_3$ | 2 | TBAB | 2 | 75 | 79 |

Based on the results summarized in Table 3, even at low temperature, the catalyst system of the disclosure provided good conversion rate of cyclic carbonate.

The effects of using different organic phosphine ligands in the catalyst system on the conversion rate of cycle carbonate are described in Example 5 and Examples 11 to 16 below.

EXAMPLES 5, 11 to 16

An epoxy compound (1,4-butanediol diglycidyl ether, BDGE, 15 g), cobalt acetate tetrahydrate ($Co(OAc)_2 \cdot 4H_2O$, 92 mg), tetrabutylammonium bromide (TBAB, 239 mg) and various types of organic phosphine ligand were placed in a reactor, followed by sealing the reactor. Similar to Example 1, the reaction was carried out for 4 hours and the product was removed from the reactor after the reactor had returned to room temperature and atmospheric pressure. The conversion rate of cyclic carbonate of the product was analyzed by $^1H$ NMR spectrum and is recorded in Table 4.

TABLE 4

(the addition amount of $Co(OAc)_2 \cdot 4H_2O$ was 10 mmol % of the epoxy compound)

| Example | Organic Phosphine Ligand Type | Molar ratio | Halogen-Containing Compound Type | Molar Ratio | Reaction Temp (° C.) | Conversion Rate (%) |
|---|---|---|---|---|---|---|
| 5 | $PPh_3$ | 2 (194 mg) | TBAB | 2 | 90 | >99 |
| 11 | $OPPh_3$ | 2 (206 mg) | TBAB | 2 | 90 | 85 |
| 12 | PPO | 2 (287 mg) | TBAB | 2 | 90 | 86 |
| 13 | $PCy_3$ | 2 (208 mg) | TBAB | 2 | 90 | 85 |
| 14 | TTPTTBP | 2 (480 mg) | TBAB | 2 | 90 | 80 |
| 15 | $P(OPh_3)_3$ | 2 (230 mg) | TBAB | 2 | 90 | 91 |
| 16 | $MePPh_2$ | 2 (148 mg) | TBAB | 2 | 90 | 89 |

In Table 4, PPO in Example 12 represents (poly (dipropylene glycol) phenyl phosphite, average molecular weight is 386); $PCy_3$ in Example 13 represents a toluene solution containing 30% of tricyclohexyl phosphine ($PCy_3$); TTPTTBP in Example 14 represents Tris(2,4-di-tert-butylphenyl)phosphite.

Based on the results summarized in Table 4, good conversion rates of cyclic carbonate were achieved, even different organic phosphine ligands of the catalyst system of the disclosure were used.

The effects of using different halogen-containing compounds in the catalyst system on the conversion rate of cycle carbonate are described in Example 5 and Examples 17 to 18 below.

EXAMPLES 17 to 18

An epoxy compound (1,4-butanediol diglycidyl ether, BDGE, 15 g), cobalt acetate tetrahydrate ($Co(OAc)_2 \cdot 4H_2O$, 92 mg), triphenyl phosphine (PPh$_3$, 194 mg) and various halogen-containing compounds were placed in a reactor, followed by sealing reactor. Similar to Example 1 above, the reaction was carried out for 4 hours and the product was removed from the reactor after the reactor had returned to room temperature and atmospheric pressure. The conversion rate of cyclic carbonate of the product was analyzed by $^1$H NMR spectrum and is recorded in Table 5.

TABLE 5

(the addition amount of Co(OAc)$_2$·4H$_2$O was 10 mmol % of the epoxy compound)

| Example | Organic Phosphine Ligand | | Halogen-Containing Compound | | Reaction Temp (° C.) | Conversion Rate (%) |
|---|---|---|---|---|---|---|
| | Type | Molar ratio | Type | Molar Ratio | | |
| 5  | PPh$_3$ | 2 | TBAB | 2 (239 mg) | 90 | >99 |
| 17 | PPh$_3$ | 2 | TBAC | 2 (206 mg) | 90 | 81 |
| 18 | PPh$_3$ | 2 | TBAI | 2 (274 mg) | 90 | >99 |

In Table 5, TBAB represents tetrabutylammonium bromide; TBAC represents tetrabutylammonium chloride; TBAI represents tetrabutylammonium iodide. Based on the results summarized in Table 5, good conversion rates of cyclic carbonate were achieved even different halogen-containing compounds of the catalyst system of the disclosure were used.

The effects of using different transition metal salts in the catalyst system on the conversion rate of cyclic carbonate are described in Example 5 and Examples 19 to 23 below.

EXAMPLES 19 to 23

An epoxy compound (1,4-butanediol diglycidyl ether, BDGE, 15 g), triphenyl phosphine (PPh$_3$, 194 mg) and tetrabutylammonium bromide (TBAB, 239 mg) and different transition metal salts were placed in a reactor, followed by sealing the reactor. Similar to Example 1 above, the reaction was conducted for 4 hours and the product was removed from the reactor after the reactor had return to room temperature and atmospheric pressure. The conversion rate of the cyclic carbonate of the product was analyzed by $^1$H NMR spectrum and was recorded in Table 6.

TABLE 6

(the amount of transition metal salts was 10 mmol % of the epoxy compound)

| Example | Transition Metal Salt | Organic Phosphine Ligand | | Halogen-Containing Compound | | Reaction Temperature (° C.) | Conversion Rate (%) |
|---|---|---|---|---|---|---|---|
| | | Type | Molar ratio | Type | Molar Ratio | | |
| 19 | RhCl$_3$    | PPh$_3$ | 2 | TBAB | 2 | 90 | 85 |
| 20 | Pd(OAc)$_2$ | PPh$_3$ | 2 | TBAB | 2 | 90 | 90 |
| 21 | Zn(OAc)$_2$ | PPh$_3$ | 2 | TBAB | 2 | 90 | >99 |
| 22 | RuCl$_2$    | PPh$_3$ | 2 | TBAB | 2 | 90 | 88 |
| 23 | FeCl$_2$    | PPh$_3$ | 2 | TBAB | 2 | 90 | 91 |

Based on the results summarized in Table 6, good conversion rates of cyclic carbonate were achieved, even different transition metal salts of the catalyst system of the disclosure were used.

According to the disclosure, a highly effective catalyst system is formed with the application of an organic phosphine ligand and a transition metal salt, and the resulting catalyst system allows carbon dioxide and an epoxy compound to undergo a cyclo-addition reaction under a moderate reaction condition for generating a cyclic carbonate compound with high yield. The catalyst system can further include a halogen-containing compound. Further, the catalyst system of the disclosure is precluded from using expensive metal ions for the reaction; hence, the cyclic carbonate produced is readily be used as raw material for the fabrication of polycarbonate resin, abrogating the requisite of recycling the catalyst.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A process to produce cyclic carbonate comprising:
   supplying an epoxy compound and carbon dioxide to a reactor to be in contact with a catalyst system to form a cyclic carbonate compound, wherein based on an used amount of the epoxy compound as a calculation standard, an used amount of the catalyst system is 1 mmol % to 50 mmol %, and
   the catalyst system comprises a transition metal salt and an organic phosphine ligand, wherein the transition metal salt comprises a halo group, an acetate group, or a combination thereof, and a molar ratio of the organic phosphine ligand to the transition metal salt is greater than 0 and less than or equal to 50.

2. The process of claim 1, wherein a reaction temperature is lower than 100° C.

3. The process of claim 1, wherein a pressure of the carbon dioxide is 1 to 20 atm.

4. The process of claim 1, wherein a reaction time is between 1 to 20 hours.

5. The process of claim 1, wherein the epoxy compound comprises 1,4-butanediol diglycidyl ether (BDGE), 1,4-cyclohexanedimethanol diglycidyl ether (CHDDG), or trimethylolpropane triglycidyl ether (TMPTGE).

6. The process of claim 1, wherein the organic phosphine ligand in the catalyst system comprises triphenyl phosphine (PPh$_3$), triphenyl phosphine oxide (OPPh$_3$), Poly(dipropylene glycol) phenyl phosphite, tricyclohexyl phosphine (PCy$_3$), Tris (2,4-di-tert-butylphenyl) phosphite, triphenyl phosphite, or diphenylmethyl phosphine.

7. The process of claim 1, wherein the transition metal salt in the catalyst system comprises Co(OAc)$_2$, Zn(OAc)$_2$, Pd(OAc)$_2$, Fe(OAc)$_2$, Fe(OAc)$_3$, Cu(OAc)$_2$, Cs(OAc), Rh(OAc)$_2$(dimer), Pb(OAc)$_2$, Sb(OAc)$_3$, La(OAc)$_3$, Bi(OAc)$_3$, Cd(OAc)$_2$, Y(OAc)$_3$, or Sc(OAc)$_3$.

8. The process of claim 1, wherein the catalyst system further comprises a halogen-containing compound.

9. The process of claim 8, wherein a molar ratio of the halogen-containing compound to the transition metal salt is greater than 0 but less than or equal to 50.

10. The process of claim 8, wherein the halogen-containing compound comprises tetrabutylammonium chloride (TBAC), tetrabutylammonium bromide (TBAB), tetrabutylammonium iodide (TBAI), anilinium chloride, benzalkonium chloride, benzoxonium chloride, cetrimonium chloride, cetylpyridinium chloride, choline chloride, didecyl dimethyl ammonium chloride, dimethyl dioctadecyl ammonium chloride, stearalkonium chloride, tetraethylammonium bromide, domiphen bromide, benzododecinium bromide, (1-ethoxy-1-oxohexadecan-2-yl)-trimethylazanium bromide, cetrimonium bromide, emepronium bromide, tetrabutylammonium tribromide, tetraoctylammonium bromide, thonzonium bromide, dithiazanine iodide, methiodide, or tetraethylammonium iodide.

11. The process of claim 1, wherein the transition metal salt in the catalyst system comprises $CoBr_2$, $RhCl_3$, $RuCl_2FeCl_2$, $FeCl_3$, $AlC_3$, $TiCl_4$, $PdX_n$, $ScX_2$, $ScX_3$, $VX_n$, $ZnX_2$, $CuX_2$, $SnX_2$, $ZrX_n$, $MoX_n$, $WX_n$, $PtX_{n, \, or \, BiXn}$, wherein X represents chlorine, bromine, or iodine, n is greater than 1 and less than or equal to 6.

* * * * *